(12) United States Patent
Pouwels et al.

(10) Patent No.: US 6,830,901 B1
(45) Date of Patent: Dec. 14, 2004

(54) PROPIONIBACTERUIM VECTOR

(75) Inventors: Pieter Hendrik Pouwels, Rijswijk (NL); Nicole Van Luijk, Utrecht (NL); Johannes P. M. Jore, Gouda (NL); Rudolf G. M. Luiten, Leiden (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 09/720,583

(22) PCT Filed: Jun. 25, 1999

(86) PCT No.: PCT/EP99/04416

§ 371 (c)(1),
(2), (4) Date: Jun. 25, 2001

(87) PCT Pub. No.: WO99/67356

PCT Pub. Date: Dec. 29, 1999

(30) Foreign Application Priority Data

Jun. 25, 1998 (EP) ............................................ 98305033

(51) Int. Cl.[7] .......................... C12P 19/42; C12N 15/00; C12N 1/20; C07H 21/02; C07H 23/00
(52) U.S. Cl. ................... 435/86; 435/320.1; 435/252.3; 435/252.55; 536/23.1; 536/26.4
(58) Field of Search ............................... 435/86, 252.3, 435/320.1, 252.33; 536/23.1, 26.4

(56) References Cited

U.S. PATENT DOCUMENTS 5,545,538 A * 8/1996 Asahi et al. .................. 435/86

FOREIGN PATENT DOCUMENTS

| EP | 0 400 931 A1 | 5/1990 | ........... C12N/15/74 |
|---|---|---|---|
| JP | 08 56673 | 3/1996 | ........... C12N/15/09 |
| WO | WO 99/67356 A3 | 12/1999 | ........... C12N/15/31 |

OTHER PUBLICATIONS

Jore J. P. et al. Efficient transformation system for Propionibacterium freudenreichii based on a novel vector, Applied and Environmental Microbiol. (2001), 67/2, 499–503.*

Rehberger and Glatz, "Characterization of Propionibacterium Plasmids", Applied and Environmental Microbiology, Apr. 1990, pp. 864–871.

Rehberger and Glatz, "Isolation of Plasmid DNA in Propionibacterium", Abstracts of the 85th annual meeting of the American Society for Microbiology, 1985, p. 20.

Rehberger and Glatz, Plasmide Associated Cell Aggregation in Propionibacterium jensenii, Abstracts of the 89th annual meeting of the American Society for Microbiology, 1989, p. 38.

* cited by examiner

Primary Examiner—Rebecca A. Prouty
Assistant Examiner—Malgorzata A. Walicka
(74) Attorney, Agent, or Firm—Morrison & Foerster LLP (57) ABSTRACT

An endogenous plasmid of *Propionibacterium* is described, isolated from *Propionibacteria freudenreichii* LMG 16545 (deposited as CBS 101022), and its sequence provided. This plasmid can be used to transform Propionibacteria to express homologous or heterologous proteins, in the production of recombinant proteins or products of enzymes, for example vitamin $B_{12}$.

8 Claims, 3 Drawing Sheets

PROPIONIBACTERUIM VECTOR

This invention relates an erogenous plasmid of *Propionibacterium*, derived from it and the use of these vectors to express (heterologous) proteins in bacteria, especially Propionibacteria. In particular transformed bacteria can be used either to produce, by fermentation, vitamin $B_{12}$ or in cheese making.

INTRODUCTION

*Propionibacterium* Gram-positive bacteria capable of producing various useful compounds in a variety of industrial processes. For example several *Propionibacterium* species are known to produce vitamin $B_{12}$ (cobalamin) in large scale fermentation processes. Other species are used in dairy applications such as cheese where they contribute, and in many cases even are mainly responsible, for the specific flavour and texture of the cheese. Many *Propionibacterium* species are considered safe for inclusion, as live organisms, into food and animal feed.

To be able to fully exploit the biotechnological potential of *Propionibacterium*, efficient and flexible genetic engineering techniques are required. Such techniques rely on the availability of a suitable plasmid to express a protein from a heterologous gene in *Propionibacterium*.

EP-A0400931 (Nippon Oil) refers to an endogenous plasmid (pTY-1) from *Propionibacterium pentosaceum* (ATCC 4875) but does not describe its sequence or exemplify how it may be used to express a heterologous gene.

JP 08-56673 refers to the plasmid pTY-1 for producing vitamin $B_{12}$ but does not provide any evidence that the plasmid remains as a freely replicating extrachromosomal element nor that the plasmid is stable inside the transformed cells.

The invention therefore seeks to provide vectors that are more efficient than those in the prior art, and can remain extrachromosomal and/or are stable. In particular the invention aims to provide an efficient vector for the cloning or expression of *Propionibacterium* or foreign genomic fragments or genes into a (*line 821*) host strain. This may enable host specific restriction enzymes to be circumvented and thereby avoid the host treating the plasmid as a foreign polynucleotide.

SUMMARY OF THE INVENTION

Accordingly, the present invention in a first aspect provides a polynucleotide comprising a sequence capable of hybridising selectively to
  (a) SEQ ID NO: 1 or the complement thereof
  (b) a sequence from the 3.6 kb plasmid of *Propionibacterium freudenrsichii* CBS 101022;
  (c) a sequence from the 3.6 kb plasmid of *Propionibacterium freudenreichii* CBS 101023; or
  (d) a sequence that encodes a polypeptide of the invention, such as (at least part of) the amino acid sequence of SEQ ID NO: 2 or SEQ ID No: 3, or the complement thereof.

SEQ ID NO: 1 sets out the DNA sequence of the endogenous plasmid of *Propionibacterium* LMG 16545 which the inventors have discovered. The first coding sequence runs from nucleotide 273 to nucleotide 1184 and the predicted amino acid sequence of this coding sequence is shown in SEQ ID NO. 2. The second coding sequence runs from nucleotides 1181 to 1493 and the predicted amino acid sequence of this coding sequence is shown in SEQ ID No: 3.

The inventors screened a large collection of *Propionibacterium* isolates and identified two strains both harboring cryptic plasmids with a size of 3.6 kb. One of the strains is *Propionibacterium freudenreichii* LMG 16545 which was deposited at Centraalbureau voor Schimmolcultures (CBS), Oosterstraat 1, Postbus 273, NL-3740 AG Baarn Netherlands, in the name of Gist-brocades B. V. of Wateringseweg 1, P.O. Box 1, 2600 MA Delft, The Netherlands, on 19 Jun. 1998 under the terms of the Budapest Treaty and was given accession number CBS 101022. The other strain is *Propionibacterium freudenreichii* LMG 16546 which was also deposited by the same depositor 19 Jun. 1998 under the terms of the Budapest Treaty at CBS and was given accession number CBS 101023.

Through full characterization and computer assisted analysis of the nucleotide sequence of LMG 16545 the inventors have been able to identify insertion sites for foreign DNA fragments. These sites have allowed construction of plasmids that are still capable of autonomous replication in *Propionibacterium*.

Surprisingly it was found that an erythromycin resistance gene from the actinomycete *Saccharopolyspora erythraea* is efficiently expressed in *Propionibacterium* and thus can be used as a selection marker for transformed cells.

Also constructed are bifunctional vectors, stably maintainable and selectable in both *E. coli* and *Propionibacterium*. This allows the use of *E. coli* for vector construction, as well as functional expression of homologous or heterologous genes in *Propionibacterium*. Vector construction using *E. coli* is comparatively easy and can be done quickly.

The polynucleotide of the invention may be autonomously replicating or extrachromosomal, for example in a bacterium such as a *Propionibacterium*.

Hence another aspect the invention provides a vector which comprises a polynucleotide of the invention.

The invention also provides a process for the preparation of a polypeptide, the process comprising cultivating a host cell transformed or transfected with a vector of the invention under conditions to provide for expression of the polypeptide.

The invention additionally provides a polypeptide which comprises the sequence set far out in SEQ ID NO: 2 or 3 or a sequence substantially homologous to that sequence, or a fragment of either sequence, or a protein encoded by a polynucleotide of the invention.

DETAILED DESCRIPTION OF THE INVENTION

Polynucleotides

A polynucleotide of the invention may be capable of hybridising selectively with the sequence of SEQ ID NO: 1, or a portion of SEQ ID No: 1, or to the sequence complementary to that sequence or portion of the sequence. The polynucleotide of the invention may be capable of hybridising selectively to the sequence of the 3.6 kb plasmid of *P. freudenreichii* CBS 101022 or CBS 101023, or to a portion of the sequence of either plasmid. Typically, a polynucleotide of the invention is a contiguous sequence of nucleotides which is capable of selectively hybridizing to the sequence of SEQ ID. No: 1 or of either 3.6 kb plasmid, or portion of any of these sequences, or to the complement of these sequences or portion of any of these sequences.

A polynucleotide of the invention and the sequence of SEQ ID NO: 1, or either of the 3.6 kb plasmids, or a sequence encoding a polypeptide, or a portion of these sequences, can hybridize at a level significantly above background. Background hybridization may occur, for example, because of other polynucleotides present in the preparation. The signal level generated by the interaction between a polynucleotide of the invention and the sequence of SEQ ID NO: 1 or of either 3.6 kb plasmid, or portion of these sequences, is typically at least 10 fold, preferably at least 100 fold, as intense as interactions between other polynucleotides and the coding sequence of SEQ ID NO: 1 or of either 3.6 kb plasmid, or a sequence encoding the polypeptide, or portion of these sequences. The intensity of interaction may be measured for example, by radiolabelling the probe, e.g. with $^{32}$P. Selective hybridisation is typically achieved using conditions of medium stringency (for example 0.3M sodium chloride and 0.03M sodium citrate at about 50° C.) to high stringency (same conditions but at about 60° C.). Polynucleotides included in the invention can be generally at least 70%, preferably at least 80 or 90%, more preferably at least 95%, and optimally at least 98% homologous (to the sequence (a) to (d)) over a region of at least 20, preferably at least 30, for instance at least 40, 60 or 100 or more contiguous nucleotides.

Any combination of the above mentioned degrees of homology and minimum sizes may be used to define polynucleotides of the invention, with the more stringent combinations (i.e. higher homology over longer lengths) being preferred. Thus for example a polynucleotide which is at least 80% or 90% homologous over 25, preferably over 30 nucleotides forms one embodiment of the invention, as does a polynucleotide which is at least 90 or 95% homologous over 40 nucleotides.

The portions referred to above may be the coding sequences of SEQ ID No: 1 or of either 3.6 kb plasmid. Other preferred portions of SEQ ID No: 1 are the replication origin, promoter or regulatory sequences, or sequences capable of effecting or assisting autonomous replication in a host cell, such as a *Propionibacterium*.

It has been found that the portion of the plasmid from the restriction site SalI to AlwNI appears to be the region that is required for replication of the plasmid. Other parts of the plasmid have been deleted and yet replication does not appear to have been adversely affected. Therefore in the invention sequence (b) and (c) can be the region delineated by the restriction sites SalI and AlwNI. This is approximately 1.7b in length. Alternatively, sequences (b) or (c) can be replaced by the sequence corresponding to nucleotides 1 to 1,800, such as 100 to 1,700, suitably 150 to 1,500, advantageously 200 to 1,300 and optimally 250 to 1,200 of SEQ. ID. No. 1. The proteins (SEQ. ID. Nos. 2 and 3) encoded by ORF1 and ORF2 respectively, are thought to both help the plasmid replicate. The plasmid replicates by the known rolling circle replication method where the original ds DNA plasmid is cut by either of the proteins which assists production of a copy of the outer strand using the inner strand as a template. The copy of the outer ring is removed and the ends joined. The host then replicates a new inner ring Using the generated outer ring as a template.

The coding sequences of the invention may be modified by nucleotide substitutions, for example from 1, 2 or 3 to 10, 25, 50 or 100 substitutions. The polynucleotides of sequence (a) to (d) may alternatively or additionally be modified by one or more insertions or deletions and/or by an extension at either or both ends. Degenerate substitution may be made and/or substitutions may be made which would result in a conservative amino acid substitution when the modified sequence is translated, for example as discussed later with relation to the polypeptides of the invention.

Polynucleotides of the invention may comprise DNA or RNA. They may also be polynucleotides which include within them synthetic or modified nucleotides. A number of different types of modification to polynucleotides are known in the art. These include methylphosphonate and phosphorothioate backbones, addition of acridine or polylysine chains at the 3' and/or 5' ends of the molecule. For the purposes of the present invention, it is to be understood that the polynucleotide described herein may be modified by any method available in the art. Such modifications may be carried out in order to enhance in vivo activity or lifespan.

Polynucleotides of the invention may be used as a primer, e.g. a PCR (polymerase chain reaction) primer, a primer for an alternative amplification reaction, a probe e.g. labelled with a revealing label by conventional means using radioactive or non-radioactive labels, or the polynucleotides may be incorporated or cloned into vectors.

Such primers, probes and other fragments will be at least 15, preferably at least 20, for example at least 25, 30 or 40 nucleotides in length. They will typically be up to 40, 50, 60, 70, 100 or 150 nucleotides in length. Probes and fragments can be longer than 150 nucleotides, for example up to 200, 300, 500, 1,000 or 1,500 nucleotides in length, or even up to a few nucleotides, such as 5 or 10 nucleotides, short of any of the sequence (a) to (d).

Polynucleotides such as a DNA polynucleotide and primers according to the invention may be produced recombinantly, synthetically, or by any means available to those of skill in the art. They may also be cloned by standard techniques. The polynucleotides are typically provided in isolated and/or purified form.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR cloning techniques. This will involve making a pair of primers (e.g. of about 15–30 nucleotides) to the region of SEQ. ID No: 1 or of either 3.6 kb plasmid which it is desired to clone, bringing the primers into contact with DNA obtained from a *Propionibacterium*, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be clone into a suitable cloning vector. Such techniques may be used to obtain all or part of SEQ ID No: 1 or either 3.6 kb plasmid.

The techniques mentioned herein are well known in the art[10].

Polynucleotides which are not 100% homologous to SEQ ID No: 1 or either 3.6 kb plasmid but fall within the scope of the invention can be obtained in a number of ways.

Homologous polynucleotides of SEQ ID NO: 1 or of either 3.6 kb plasmid may be obtained for example by probing genomic DNA libraries made from a range of Propionibacteria, such as *P. freudenreichii*, *P. jensenii*, *P. thoenii*, *P. acidipropiloici*, or other strains of bacteria of the class Actinomycetes, or other gram positive bacteria, or those that are G: C rich. All these organisms are suitable sources of homologous or heterologous genes, promoters, enhancers, or host cells, for use in the invention.

Such homologues and fragments thereof in general will be capable of selectively hybridizing to the coding sequence of SEQ ID NO: 1 or its complement or of either 3.6 kb plasmid. Such sequences may be obtained by probing genomic DNA libraries of the *Propionibacterium* with probes comprising all or part of the coding sequence SEQ ID NO: 1 or of either 3.6 kb plasmid under conditions of medium to high stringency (for example 0.03M sodium chloride and 0.3M sodium citrate at from about 50° C. to about 60° C.).

Homologues may also be obtained using degenerate PCR which will use primers designed to target conserved sequences within the homologues. Conserved sequences can be predicted from aligning SEQ ID No: 1 or the sequence of either 3.6 kb plasmid with their homologues. The primers will contain one or more degenerate positions and will be used at stringency conditions lower than those used for cloning sequences with single sequence primers against known sequences.

Alternatively, such polynucleotides may be obtained by site directed mutagenesis of SEQ ID No: 1 or of either 3.6 kb plasmid, or their homologues. This may be useful where for example silent codon changes are required to sequences to optimise codon preferences for a particular host cell in which the polynucleotide sequences are being exposed. Other sequences may be desired in order to introduce restriction enzyme recognition sites or to alter the property or function of the polypeptides encoded by the polynucleotides.

Methods of measuring polynucleotide homology are well known in the art. For example the UWGCO package provides the BESTFIT programme which can be used to calculate homology, for example used on its default setting[7]. For amino acid homology with regard to polypeptides of the invention which are discussed later, one can employ BLAST (Basic Local Alignment Search Tool[1]), which produces alignments of amino acid sequences (and nucleotide sequences if necessary) to determine sequence similarity. BLAST can thus be used to determine exact matches or to identify homologues, and is particularly used for those matches which do not contain gaps. The BLAST technique uses the algorithm based on the High-scoring Segment Pair (HSP).

The invention includes double sided polynucleotides comprising a polynucleotide sequence of the invention and its complement.

Polynucleotides (e.g. probes or primers) of the invention may carry a revealing label. Suitable labels include radio-isotopes such as $^{32}P$ or $^{35}S$, enzyme labels, or other protein labels such as biotin. Detection techniques for these labels are known per se.

The polynucleotides (labelled or unlabelled) may be used in nucleic acid-based tests for detecting or sequencing another polynucleotide of the invention, in a sample.

Polynucleotides of the invention include variants of the sequence of SEQ ID 1 or of either 3.6 kb plasmid which are capable of autonomously replicating or remaining extrachromosomally in a host cell. Such variants may be stable in a bacterium such as a Propionibacterium.

Generally the polynucleotide will comprise the replication origin and/or coding region(s) of SEQ ID No: 1 or of either 3.6 kb plasmid, or homologues of these sequences. A polynucleotide of the invention which is stable in a host cell such as Propionibacterium, or E. coli is one which is not lost from the host within five generations, such as fifteen generations, preferably thirty generations. Generally such a polynucleotide would be inherited by both daughter cells every generation.

The polynucleotide may comprise a promoter or an origin of replication (e.g. upstream of any sequences encoding a replication protein).

The polynucleotide of the invention can be transformed or transfected into a bacterium, such as a Propionibacterium, or E. coli, for example by a suitable method[11]. It may be present in a bacterium at a copy number of 5 to 500, such as 10 to 100.

The polynucleotide may be capable of autonomous replication in a bacterium other than a Propionibacterium. Such a bacterium may be E. coli or a gram positive or G:C rich bacterium or one of the class Actinomycetes. Such a polynucleotide will generally comprise sequences which enable the polynucleotide to be autonomously replicated in that bacterium. Such sequences can be derived from plasmids which are able to replicate in that bacterium.

A polynucleotide of the invention may be one which has been produced by replication in a Propionibacterium. Alternatively it may have been produced by replication in another bacterium such as E. coli. The polynucleotide may be able to circumvent the host restriction systems of Propionibacterium.

Vectors

A second aspect of the invention relates to a vector comprising a polynucleotide of the first aspect. The vector may be capable of replication in a host cell, such as a bacterium, for examples Actinomycetes, e.g. Propionibacterium or, E. coli. The vector may be a linear polynucleotide or, more usually, a circular polynucleotide. The vector may be a hybrid of the polynucleotide of the invention and another vector. The other vector may be an E. coli vector, such as pBR322, or a vector of the pUC family, R1, ColD or RSF1010 or a vector derived therefrom.

The polynucleotide or vector of the invention may be a plasmid. Such a plasmid may have a restriction map the same as or substantially similar to the restriction maps shown in FIG. 1, 2a or 2b.

The polynucleotide or vector may have a size of 1 kb to 20 kb, such as from 2 to 10 kb, optimally from 3 to 7 kb.

The polynucleotide or vector may comprise multiple functional cloning sites. Such cloning sites generally comprise the recognition sequence of restriction enzymes. The polynucleotide or vector may comprise the sequence shown in SEQ ID No: 1 and/or contains restriction enzyme recognition sites for EcoRI, SacI, AlwNI, BsmI, BsaBI, BclI, ApaI, HindIII. SalI, HpaI, PstI, SphI, BamHI, A651, EcoRV and BglII. The polynucleotide or vectors may thus comprise one, more than one or all of these restriction enzyme sites, generally in the order shown in the Figures.

Preferably, when present in a bacterium such as a Propionibacterium or E. coli, the polynucleotide or vector of the invention does not integrate into the chromosome of the bacterium. Generally the polynucleotide or vector does not integrate within 5 generations, preferably 20 or 30 grunions.

The polynucleotide or vector may be an autonomously replicating plasmid that can remain extrachromosomal inside a host cell, which plasmid is derived from an (to the host) is capable of expressing that gene inside the host cell. The term "derived from" means that the autonomously replicating plasmid includes a sequence the same as the polynucleotide of the invention.

The vector of the invention may comprise a selectable marker. The selectable marker may be one which confers antibiotic resistance, such as ampicillin kanamycin or teracylin resistance genes. The selectable marker may be an erythromycin resistance gene. The erythromycin resistance gene may be from Actinomycetes such as *Saccharopolyspora erythraea*, for example from *Saccharopolyspora erythraea* NRKL2338. Other selectable markers which may be present in the vector include genes conferring resistance to chloraphenicol, thiostreptomycin, viomycin, ncomycin apramycin, hygromycin, bicomycin or streptomycin.

The vector may be an expression vector, and so may comprise a heterologous gene (which does not generally occur in the host cell, e.g. Propionibacteria), or an endogenous or homologous gene of the host e.g. Propionibacteria. In the expression vector the gene to be expressed is usually operably linked to a control sequence which is capable of providing for the expression of the gene in a host cell.

The term "operably linked" refers to a juxtaposition wherein the components described are in a relationship permitting them to function in their intended manner. A controlled sequence "operably linked" to a coding sequence is ligated in such a way that expression of the coding sequence is achieved under conditions compatible with the control sequences.

The heterologous or endogenous gene may be inserted between nucleotides 1 and 200 or between nucleotides 1500 to 3555 of SEQ ID No:1 or at an equivalent position in a homologous polynucleotide.

Such genes may comprise homologous or endogenous genes such as for elongation factors, promoters regulatory sequences or elements, and replication proteins. Other genes (which may be heterologous to the host) include those encoding for or assisting in the production of nutritional factors immmomodulators, hormones, proteins and enzymes (e.g. protease, amylases, peptidases, lipases), texturing agents, flavouring substances (e.g. diactyl, actonc), gene clusters antimicrobial agents (e.g. nisin), substances for use in foodstuffs (e.g. in sausages, cheese) metabolic enzymes, vitamins (e.g. $B_{12}$), uroporphyrinogen (III) methyltransferase (UP III MT), cobA, antigens and (e.g. for vaccines) therapeutic agents. As will be seen the hosts can produce a wide variety of substance not just polypeptides, which may be either the desired product or may be used to produce the desired product.

The heterologous gene may have a therapeutic effect on a human or animal. Such a gene may comprise an antigen for example from a pathogenic organism. The host, such as *Propionibacterium*, comprising a polynucleotide with such a heterologous gene may be used as or in a vaccine, and may provide protection against the pathogens.

The heterologous antigen may be a complete protein or a part of a protein containing an epitope. The antigen may be from a bacterium, a virus, a yeast or a fungus.

Host Cells and Expression

The host cell forms the third aspect of the invention and comprise a polynucleotide or vector of the first or second aspect. The host cell may be a bacterium e.g. of the class Actinomrycetes. The bacterium may be a *Propionibacterium* or *E. coli*. The *Propionibacterium* may be *P. freudenreichii, P. jensenii, P. thoenii* or *P. acidipropionici*.

In a fourth aspect the invention provides a process for producing a host cell of the third aspect, the process comprising transforming or transfecting a host cell with a polynucleotide or vector of the first or second aspect, e.g. with known formation techniques[11].

In a fifth aspect the invention provides a process for the preparation of a polypeptide encoded by the polynucleotide or vector of invention present in host cell of the invention comprising placing or culturing the host cell in conditions where expression of the polypeptide occur.

This aspect of the invention thus provides a process for the preparation of a polypeptide encoded by a given gene, which process comprises cultivating a host cell transformed or transfected with an expression vector comprising the gene, under conditions to provide for an expression of the said polypeptide, and optionally recovering the expressed polypeptide. The host cell may be of the class Actinomycetes, or a gram positive bacteria such as *Propionibacterium* or *E. coli*.

Promoters, translation initiators, translation terminators, elongation factor genes, ribosomal. RNA, antibiotic resistance genes, synthetic promoters (e.g. designed on consensus sequences) to other expression regulation signals present in the polynucleotide or vector can be those which are compatible with expression in the host cell. Such promoters include the promoters of the endogenous gene: of the host coll.

Culturing conditions may be aerobic or anaerobic conditions depending an the host. For a fermentation process the host cell would be placed in anaerobic, and then possibly aerobic conditions. The compound produced, such as an exposed polypeptide, may then be recovered, e.g. from the host cell or fermentation medium. The expressed polypeptide may be secreted from the host cell. Alternatively the polypeptide may not be secreted from the host cell. In such a case the polypeptide may be expressed on the source of the host cell. This may be desirable, for example, if the polypeptide comprises an antigen to which an immune response is desired in human or animal A homologous gene that may be present in the vector of the invention may be cobA. A host cell vector may therefore be capable of producing a compound such as vitamin $B_{12}$, from a substrate or the compound may be the product of an enzyme. The invention specifically provides a process for the preparation of vitamin $B_{12}$ comprising cultivating or fermenting such a host cell under conditions in which the UP(III) MT gene is expressed. The expressed enzyme can be contacted with a suitable substrate under conditions in which the substrate is converted to vitamin $B_{12}$. This may result in increased production of vitamin $B_{12}$.

Therapeutics

As described above the polynucleotide of the invention may comprise a heterologous gene which is a therapeutic gene. Thus the invention includes a host cell comprising a vector of the invention which comprises a therapeutic gene for use is a method of treatment of the human or animal body by therapy. Such a host cell may be *Propionibacterium*. The host cell may be alive or dead, The host cell can be formulated for clinical administration by mixing them with a pharmaceutically acceptable carrier or diluent. For example they can be formulated for topical, parenteral, intravenous, intramuscular, subcutaneous, oral or transdermal administration. The host call may be mixed with any vehicle which is pharmaceutically acceptable and appropriate for the desired route of administration. The pharmaceutically acceptable carrier or diluent for injection may be, for example, a sterile or isotonic solution such as Water for injection or physiological saline.

The dose of the host cells may be adjusted according to various parameters, especially according to the type of the host cells used, the age, weight and condition of the patient to be treated; the mode of administration used; the condition to be treated; and the required clinical regimen. As a guide, the number of host cells administered, for example by oral administration, is from $10^7$ to $10^{11}$ host cells per dose for a 70 kg adult human.

The routes of administration and dosages described are intended only as a guide since a skilled practitioner will be able to determine readily the optimum route of administration and dosage of any particular patient and condition.

Polypeptides

A six aspect of the invention provides a polypeptide of the invention comprising one of the amino acid sequences setout in SEQ ID NO: 2 or 3 or a substantially homologous sequence or of a fragment of either of these sequences, the polypeptide may be one encoded by a polynucleotide of the first aspect. In general, the naturally occurring amino acid sequences shown in SEQ ID NO: 2 or 3 are preferred. However, the polypeptides of the invention include homologues of the natural sequences, and fragments of the natural sequences and their homologues, which have the activity of the naturally occurring polypeptide. One such activity may be to effect the replication of the polynucleotide of the invention. In particular, a polypeptide of the invention may comprise:

(a) the protein of SEQ ID No: 2 or 3; or (b) a homologue thereof from Actinomycetes, such as *Propionibacterium freudenreichii* or other *Propionibacterium* strains or (c) a protein at least 70% homologous to (a) or (b).

A homologue may occur naturally in a *Propionibacterium* and may function in a substantially similar manner to a polypeptide of SEQ ID NO: 2 or 3. Such a homologue may occur in Actinomycetes or gram positive bacteria.

A protein at least 70% homologous to the protein of SEQ ID NO: 2 or 3 or a homologue thereof will be preferably at least go or 90% and more preferably at least 95%, 97% or 99% homologous thereto over a region of at least 20, preferably at least 30, for instance at least 40, 60 or 100 or more contiguous amino acids. Methods of measuring protein homology are well known in the art and it will be understood by those of skill in the art that in the present context homology is calculated on the basis of amino acid identity (sometimes referred to as "hard homology").

The sequences of the proteins of SEQ ID NO: 2 and 3 and of homologues can thus be modified to provide other polypeptides within the invention.

Amino acid substitutions may be made, for example from 1, 2 or 3 to 10, 20 or 30 substitutions. The modified polypeptide generally retains its natural activity. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Polypeptides of the invention also include fragments of the above-mentioned full length polypeptides and variants thereof, including fragments of the sequences set out in SEQ ID NO: 2 or 3. Such fragments can retain the natural activity of the full-length polypeptide.

Suitable fragments will be at about 5, e.g. 10, 12, 15 or 20 amino acids in size. Polypeptide fragments of SEQ ID No: 2 and 3 and homologues thereof may contain one or more (e.g. 2, 3, 5, or 10) substitutions, deletions or insertions, including conserved substitutions.

Polypeptides of the invention may be in a substantially isolated form. A polypeptide of the invention may also be in a substantially purified form, in which case it will generally comprise the polypeptide in a preparation in which more than 90%, e.g. 95% 98% or 99% of the polypeptide in the preparation is a polypeptide of the invention.

A polypeptide of the invention may be labelled with a revealing label. The revealing label may be any suitable label which allows the polypeptide to be detected. Suitable labels include radioisotopes, e.g. $^{125}I$, $^{35}S$, enzymes, antibodies, polynucleotides and linkers such as biotin.

INDUSTRIAL APPLICATIONS

As will be apparent from the discussion, the host cells of the third aspect can be used to produce not only the recombinant proteins, but also other compounds of interest, including non-proteins such as inorganic chemicals, in particular vitamins. A seventh aspect of the present invention therefore relates to a process for the production of a compound, the process comprising culturing or fermenting host cells of the third aspect under condition whereby the desired compound is produced. Although this compound may be a polypeptide, for example a polypeptide of the sixth aspect, it may also be one of the compounds mentioned in the previous discussion concerning genes to be expressed. Clearly inorganic compounds will not be expressed by a gene, but they may be produced by an enzyme or the polypeptide or enzyme may assist the host cell in the production of the desired compound. These compounds may be produced inside the cell, and later isolated, for example following lysis of the host call or they may pass through the wall of the host cell into a surrounding medium, which may be a fermentation medium for example an aqueous solution. In this way the host cells can be cultured in an aqueous medium that comprises cells and nutrients for the cells, for example assimiable sources of carbon and/or nitrogen.

The polypeptides so produced may have therapeutic uses. They may be drugs or other pharmacologically active compounds, or may be antigenic or immunogenic, in which case they may find use in vaccines.

The invention additionally encompasses compounds produced by this process, whether or not it is a recombinant polypeptide. Compounds specifically contemplated are vitamins, such as vitamin $B_{12}$ (cobalamin).

In some cases the compound need not be isolated either from the fermentation medium or from the host cells. The host cells may themselves be used in particular applications, for example in, or in the manufacturing of, foodstuffs such as sausages, or in cheese makings or the host cells may for example be included in an animal feed such as when the host cells contain compound to be ingested by the animal in question. The invention therefor extends to the use of these compounds or the host cells in the production of foodstuffs such as cheeses and sausages. The invention also contemplates foodstuffs or animal feed comprising host cell or a compound produced by the invention.

In a particularly preferred embodiment of the present invention the host cells can be used in a cheese making process, and so the invention additionally includes a process for manufacturing cheeses where the microorganism employed are host cells of the invention. The host cells may be used instead of or in addition to, other bacteria, such as lactic acid bacteria. Propionic acid bacteria are currently used in cheese making processes, for example with mesophilic cultures type of cheese) as well as thermophilic cultures (Emmental). Both mesophilic and thermophilic organisms can be responsible for the acidification of the milk or cheese. In this way the host cells of the invention can be not only used for cheese but also for the production of other family dairy products (e.g. yoghurts). Propionic acid bacterium are employed in cheese making because of their ability to convert lactate and carbohydrates to propionic acid, acetic acid and carbon dioxide. The host cells of the invention, especially if they are propionibacteria, can be employed because they can be less sensitive to nitrates and salt, which may allow the reduction or omission of bactofugation of the milk (usually employed to reduce the levels of Clostridia).

The fermentation of the host cells may have one or two phases or stages. These may be for example a growth and/or production phase, or anaerobic and/or aerobic phase. Preferably, there will be a growth and/or anaerobic phase, and suitable also (e.g. afterwards) a production and/or aerobic phase.

Both the carbon and/or nitrogen sources may be complex sources or individual compounds. For carbon, it is preferred that this is glucose. For nitrogen, appropriate sources include yeast extract or ammonia or ammonium ions.

Preferred features and characteristics of one aspect of the invention are suitable for another aspect mutatis mutandis.

FIGURES

The invention is illustrated by the accompanying drawings in which.

The invention will now be described, by way of example, by reference to the following Examples, which are not to be construed as being limiting.

EXAMPLE 1

Screening of *Propionibacterium* Strains

A collection of 75 nonpathogenic strains of *Propionibacterium* was screened for the presence of indigenous plasmids. The majority of strains were obtained from the BCCM/LMG culture collection (Ghet, Belgium), although some were obtained from ATCC (Rockville, Md., USA) or from DSM (Braunschweig, Germany). Screening was performed using a small scale plasmid isolation procedure. First bacteria were cultivated anaerobically in MRS medium[4] for 48 hrs at 30° C.

Plasmids were then purified from the bacteria using a plasmid DNA isolation procedure originally developed for *E. coli*[4] with some modifications: cells from a 5 ml culture were washed in a 25% sucrose, 50 mM Tris.HCl pH8 solution, resuspended in 250 µl, TENS (25% sucrose+50 mM NaCl+50 mM Tris.HCl+5 mM EDTA pH8), containing 10 mg/ml lysozyme (Boehringer Mannheim), and incubated at 37° C. for 20–30 minutes. The bacterial cells were then lysed in 500 µl of 0.2 N NaOH/1% SDS (2–5 minute incubation on ice). After addition of 400 µl 3M NaAc pH4.9 (5 minutes on ice) and a subsequent extraction with phenol/chloroform, the DNA was precipitated by addition of isopropanol.

The DNA was analysed by electrophoresis on 1% agaose gels, and visualised by ethidium bromide. Whereas most strains were negative, i.e. did not reveal the presence of indigenous plasmids in this analysis, the majority of strains that proved positive contained large (≦20 kb) plasmids. Smaller plasmids were observed in 6 strains. Of these *P. jensenii* LMG16453 *P. acidipropionici* ATCC4875. *P. acidipropianici* LM0 16447 and a nonspecified *Propionibacterium* strain (LMG16550) contained a plasmid in size range of 6–10 kb. Two (*P. freudenreichii* LMG16545 and *P. freudenreichii* LMG16546) showed an identical plasmid profile of 2 plasmid. One plasmid was large (size not determined) and the other was smaller, more abundantly present and had a size of 3.6 kb. These 3.6 kb plasmids from LMG16545 and LMG16546 were chosen for further analysis.

EXAMPLE 2

Analysis of an Indigenous Plasmid from Strains LMG 16545 and LMG16546

Figure 1:
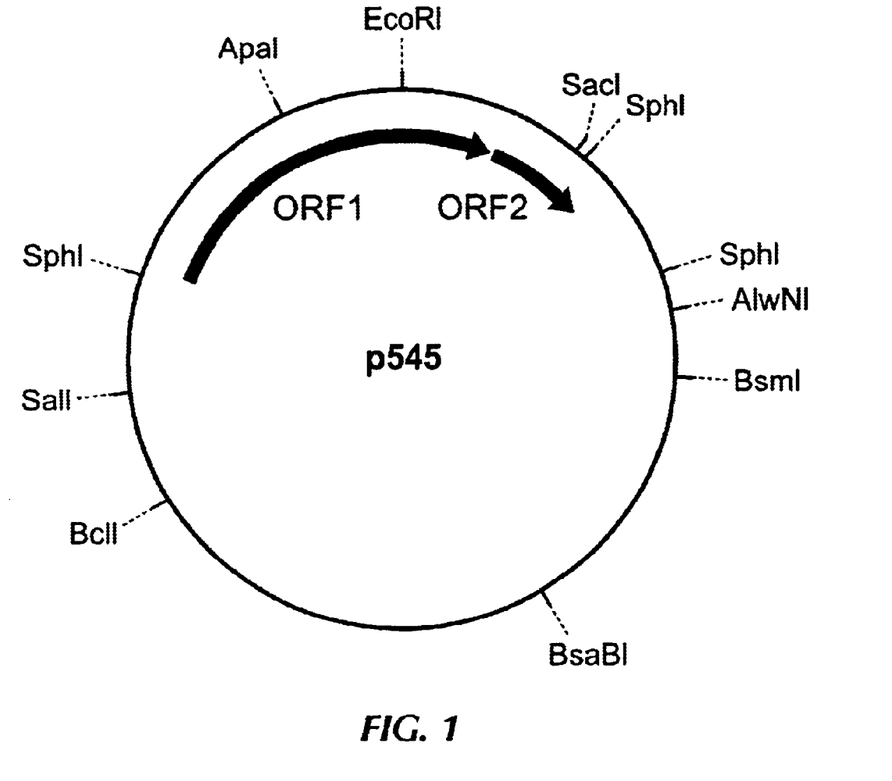
FIG. 1 is a restriction map of a vector within the invention, p545 obtained from *P. freudenreichii LMG*16545 (CBS 101022)
Figure 2A:
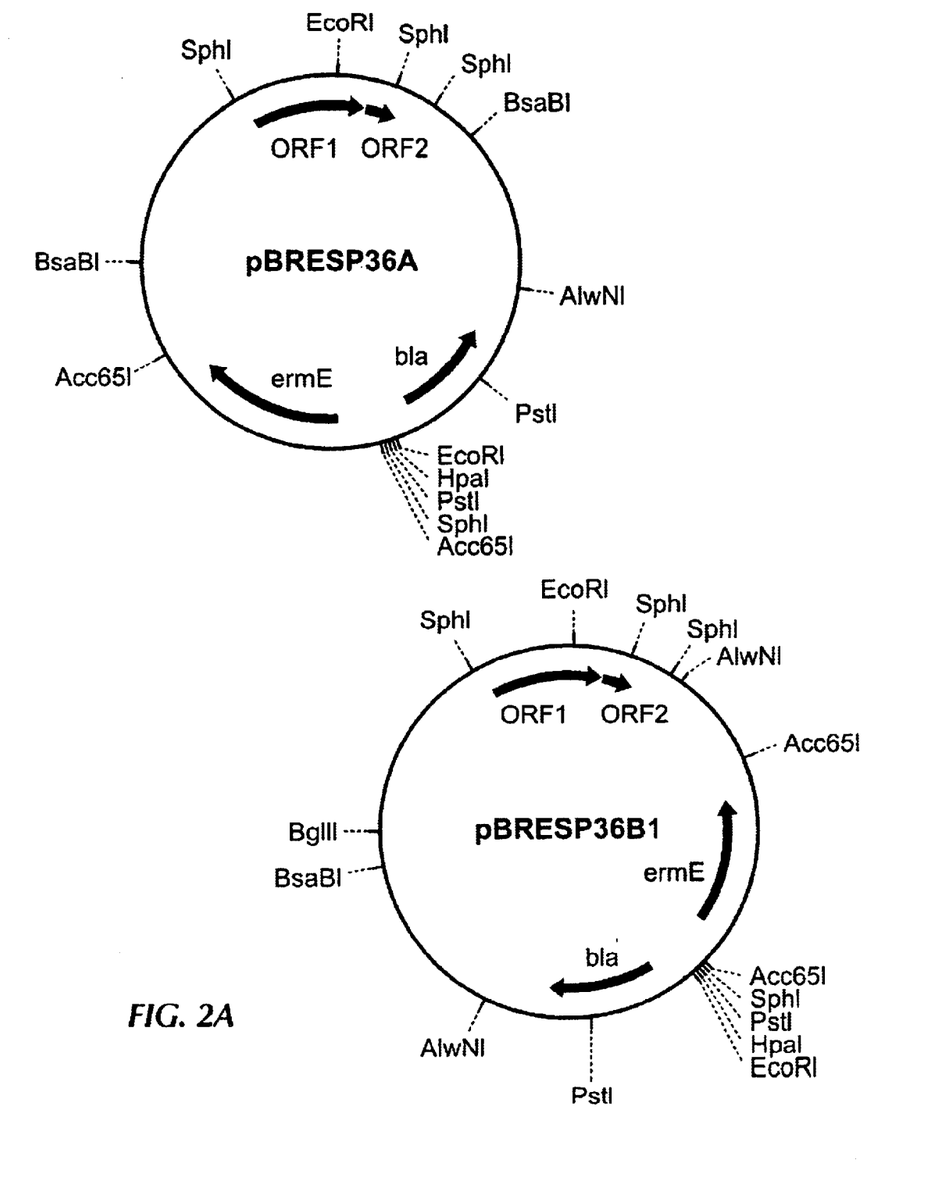
FIGS. 2a and 2b each contain two maps of two vectors, all four vectors being within the invention.
Figure 2B:
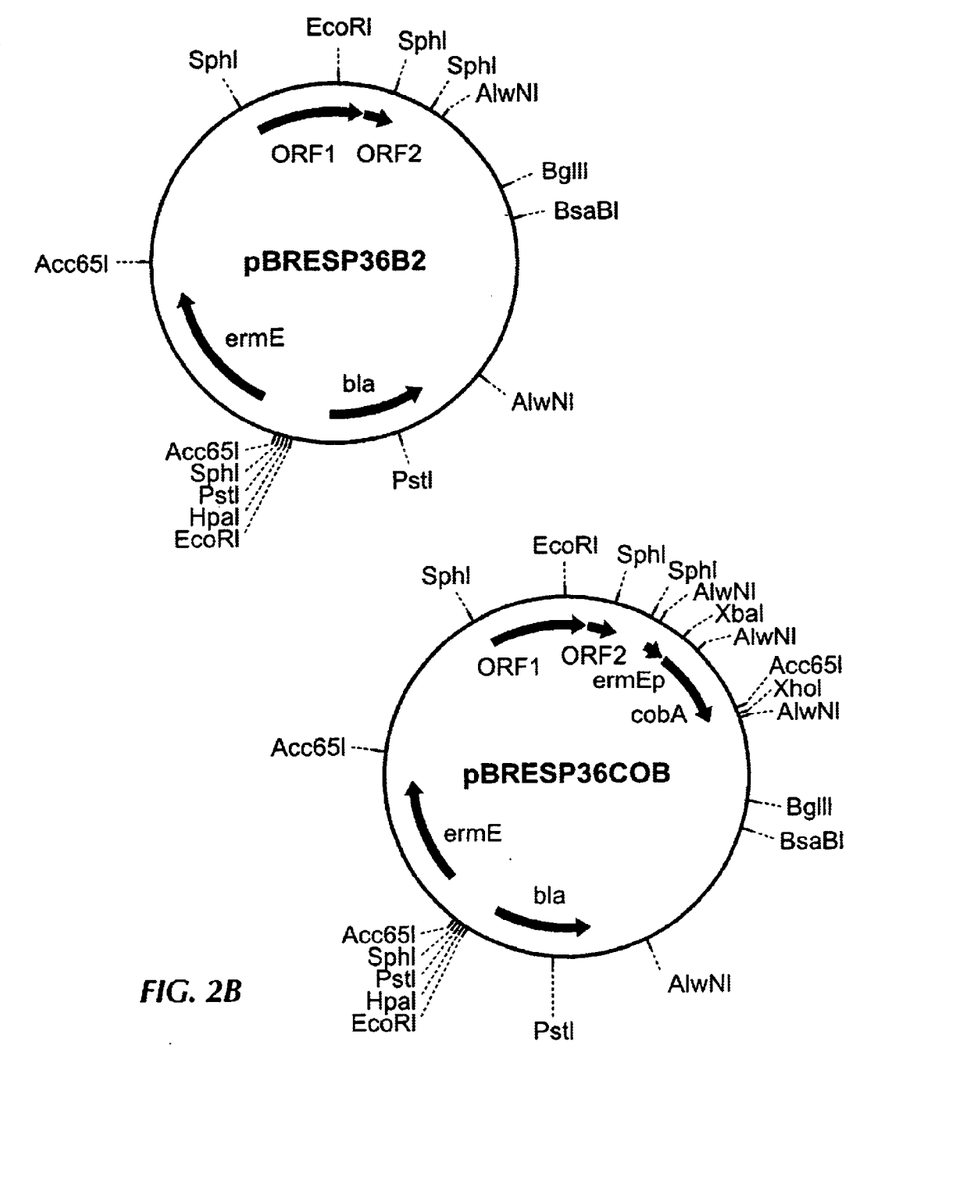

The 3.6 kb plasmids were isolated from both and further purified by CsCl-ethidium bromide density gradient ultracentrifugation[11]. Limited restriction maps were made of both preparations and these turned out to be identical.[11] The restriction map of the 3.6 kb plasmid is shown in FIG. 1. Restriction enzymes and T4 ligase were obtained from New England Biolabs or GIBCO BRL.

The 3.6 kb plasmid from strain LMG16545 (from here on referred to as p545) was radioactively labelled and used in Southern blot hybridization experiments. Hybridisation conditions were 0.2×SSC, 65° C. It reacted equally well with both LMG16545 and LMG16546 plasmid DNA extracts, supporting the close relationship of these strains whereas a plasmid DNA extmct from *P. acidipropionici* ATCC4875, that harbors a 6.6 kb plasmid called pTY1 or pRG01[8] failed to react.

The DNA sequence of plasmid p545 was determined with fluorescent dye labelled dideoxyribonucleotides in an Applied Biosystems 373A automatic sequencer and is included as SEQ ID No: 1 in the sequence listing. Sequence analysis was performed on plasmid DNA that had been linearized with EcoRI and inserted into EcoRI digested pBluescript SKII+DNA (Stratagene, La Jolla, Calif., USA). Computer assisted analysis of the sequence thus obtained using BLAST search[1] revealed homologies to protens involved in replication of plasmids from several GC-rich organisms (eg., pAL5000 encoded repA and repB from *Mycobacterium fortuitum*[8,14] show 28–30% identity and 34–38% similarity with the respective putative replication proteins from plasmid p545; pXZ10142 from *Corynebacterium glutamicum* [PIR Accession Number S32701] in another example of plasmids encoding replication proteins homologous to the p545 putative replication proteins). The results of the database comparisons with homologous sequences are detail in Examples 7 and 8.

EXAMPLE 3

Construction of *E. coli/Propionibacterium* Shuttle Vectors

*E. coli* plasmid pBR322 was dicsed with EcoRI and AvaI and the smaller fragment thus generated (measuring 1.4 kb and encompassing the tetracyclin resistance conferring gene) was replaced by a synthetic duplex DNA. The synthetic duplex DNA was designed so as to link EcoRI and AvaI ends and to supply a number of unique restriction enzyme sites:

5'-AATTCAAGCTTGTCGACGTTAACCTGCAGGCATG CGGATCCGGTACCGATATCAGATCT-3' (SEQ. ID. NO. 4)

3'GTTCGAACAGCTGCAATTGGACGGTCCGTACGCC TAGGCCATGGCTATAGTCTAGAAGCC-5' (SEQ. ID. NO. 5)

The following restriction enzyme recognition sites were supplied in this way. EcoRI (restored) HindIII, SalI, HpaI PstI SphI, BamHI, Acc65, EcoRV, BglII (AvaI is not restored).

This synthetic DNA was ligated to the large fragment and the ligation transferred back to *E. coli* (T4 ligase was used). A plasmid of the expected composition was obtained (pBR322ΔI). The multiple cloning site can be used to introduce a selection marker as well as plasmid p545 DNA. conferring resistance to erythromycin was performed as will now be described.

A 1.7 kb Acc65I fragment from the *Saccharapolyspora erythraea* NRRL2338 erythromycin biosynthesis cluster and containing the erythromyin resistance conferring gene[15,2]

was inserted into Acc65I linearized pBR322ΔI. Then the newly derived construct, named pBRES, was linearized with EcoRV and ligated to p545 DNA the had been digested with BsaBI. *E. coli* transformants were found to harbor a vector with the correct insert in both orientations. The resulting plasmid vectors were named pBRESP36B1 and pBRESP36 FIGS. 2a and 2b).

Plasmid vector constructs were also obtained with p545 DNA linearized in an other restriction site situated outside the putative replication region, namely AlwNI. For this construction the pBRES vector had to be provided with a suitable cloning site. An adaptor was designed consisting of two complementary oligonucleotides of the following composition (SEQ. ID. Nos 6 and 7):
5' GTACCGGCCGCTGCGGCCAAGCTT 3'
5' GATCAAGCTTGGCCGCAGCGGCCG 3'

Annealing of these oligo's created a double strand DNA fragment with Acc65I and BglII cohesive ends respectively, which moreover contain an internal SfiI restriction site, that provides ends compatible to the AlwNI digested p545 plasmid. This adaptor was cloned in pBRES between the Bgn and the proximal Acc65I site. The pBRE-Sfi vector thus obtained subsequently digested by SfiI and ligated to AlwNI digested p545. Transformation of *E. coli* yielded tranformants with the correct vector as confirmed by restriction enzyme analysis. The vector obtained was named pBRESP36A (FIG. 2).

EXAMPLE 4
Transformation of *Propionibacterium* with *E. coli*/ *Propionibacterium* Shuttle Vectors Transformation of *Propionibacterium freudenreichii* strain ATCC6207 with pBRESP36B1 will be described.

The bacterial cells are cultivated in SLB (sodium lactate broth[17] at 30° C. to a stationary growth phase, and subsequently diluted 1:50 in fresh SLB. After incubation at 30° C. for around 20 hours cells (now in the exponential growth phase) were harvested and washed extensively in cold 0.5M sucrose. Subsequently cells were washed once in the electroporation buffer, consisting of 0.5M sucrose, buffered by 1 mM potassiumacetate pH5.5, and finally resuspended in this electroporation buffer in about 1/100 of the original culture volume. Cells were kept on ice during the whole procedure.

For the electroporation (apparatus from BIORAD), 80–100 μl of cell suspension was mixed with ±1 μg of DNA (or smaller amounts), in a cooled 1 or 2 mm electroporation cuvette, and an electric pulse delivered. Optimal pulse conditions were found to be 25 kV/cm a 200 Ω resistance and 25 μF capacitance. However, lower and higher voltages (also at 100 Ω) also yield transformants.

Immediately after the pulse, 900 μl cold SLB containing 0.5 M sucrose was added to the pulsed cell suspension and these are subsequently incubated for 2.5 to 3 hours at 30° C. before platin appropriate dilutions on SLB/agar plates containing 0.5 M sucrose and 10 μg/ml erthomycin. After a 5 to 7 day incubation period at 30° C. under anaerobic conditions, transformants were detected.

DNA isolated from *E. coli* DH5α (Promega) yielded a transformation efficiency of 20–30 transformants per μg DNA. A 10–100 fold higher efficiency is achieved when DNA is isolated from *E. coli* JMI10 (dam⁻, dcm⁻strain). *E. coli* transformation was done according to BIORAD instructions.

Transformants contained the authentic vectors, indistinguishable from the original plasmid DNA used for transformation of ATCC6207. This was shown by restriction enzyme analysis of plasmid DNA isolated from the transformants by the small scale plasmid DNA isolation procedure referred to before.

Vectors were exclusively present as autonomously replicating plasmids. Southern blot hybridization[13] with total DNA isolates showed that chromosomal DNA did not hybridise to the vector DNA used as a probe, indicating that no chromosomal integration of plasmid DNA occurred.

Transformation was also successful with vectors pBRESP36B2 and pBRESP36A, indicating that functionality of the vector was independent of the orientation of p545 or the cloning site used. Also in this case the authenticity of the vector was confirmed.

Moreover, transformation of *P. freudenreichii* strain ATCC6207 with DNA isolated from *Propionibacterium* transformant resulted in a $10^5$–$10^6$ fold increased transformation efficiency as compared to that obtained with DNA isolated from *E. coli* DH5α.

Transformation of another *P. freudenreichii*, LMG16545 (the same stain from which the p545 plasmid was obtained), resulted in a transformation efficiency comparable to that of the ATCC strain.

The results of the transformations, and the effect on vitamin $B_{12}$ production, is shown in the following Table.

Eight out of 10 transformants gave up to a 50% higher vitamin $B_{12}$ content than the control strain.

| Strain ID | Transformed plasmid | Vitamin $B_{12}$ (mg/g dry matter) |
|---|---|---|
| COB1 | pBRES36COB | 0.57 |
| COB2 | pBRES36COB | 0.67 |
| COB3 | pBRES36COB | 0.83 |
| COB4 | pBRES36COB | 0.68 |
| COB5 | pBRES36COB | 0.69 |
| COB6 | pBRES36COB | 0.61 |
| COB7 | pBRES36COB | 0.53 |
| COB8 | pBRES36COB | 0.64 |
| COB9 | pBRES36COB | 0.50 |
| COB10 | pBRES36COB | 0.74 |
| recATCC6207 | pBRESP36B2 | 0.54 |

EXAMPLE 5
Construction of Plasmid Vector Containing cobA Gene

The construction and application of a plasmid vector to increase the level of vitamin B12, (cobalamin) synthesis in *P. freudenreichii* strain ATCC6207 will be described.

The promote region of the gene conferring erythromycin resistance in *Saccharopolyspora erythraea*[2,3] was generated by PCR using the following primers (SEQ. ID. Nos 8 and 9):
forward primer (5'-3')
AAACTGCAGCTGCTGGCTTCGCCCCGATGCTAGTC
reverse primer: (5'-3')
AAACTGCAGCAGCTGGGCAGGCCGCTGGACGGCC
TGCCCTCGAGCTCGTCTAGAATGTGCTGCCG
ATCCTGGTTGC The PCR fragment thus generated contained an AlwNI site at the 5' end followed by the authentic promoter region and first 19 amino acids of the coding region of the erythromycin resistance gene, to ensure proper transcription and translation initiation. At the 3' end XbaI and XhoI sites were provided (for insertion of the cobA gene in a later stage), a terminator sequence as present downstream from the erythromycin resistant gene, and an AlwNI site.

The PCR product was digested by AlwNI and ligated to pBRESP36B2, partially digested with AlwNI. Of the two AlwNI sites present in pBRESP36B2, only the one present in the p545 specific part of the vector will accommodate the *E. coli* transformants were obtained harboring the expected construct, named pBRES36pEt. This vector was used for further constructions as described below.

The coding sequence of cobA, the gene encoding uroporphyrinogen III methyltransferase was generated by PCR from *Propionibacterium freudenreichii* strain ATCC6207, using the following primers (SEQ. ID. Nos 10 and 11): forward: (5'-3) CTAGTCTAGACCACCGATGAGGAAACCCGATGA reverse: (5'-3) CCCAAGCTTCTCGAGTCAGTGGTCGCTGGGCGCGCG The cobA gene thus amplified carried XbaI site at the N terminal coding region, and HindIII and XhoI sites at the C terminal coding region.

The functionality of this cobA gene was confirmed by cloning the PCR product as an XbaI-HindIII fragment pUC18, and subsequent transformation of *E. coli* strain JM109. Transformants with a functional cobA gene show a bright red fluorescence when illuminated with UV light. Plasmid DNA isolated from such a transformant was digested with XbaI and XhoI, ligated to likewise digested pBRESP36B$_2$. DNA and used for transformation of *E. coli*. DNA from several transformants was analaysed by restriction enzyme digestion and gel electrophoresis Transformants were found to bear the correct insert in the expression vector. This new vector was named pBRES36COB. This vector was subsequently transferred to *P. freudenreichii* ATCC6207 following the protocol described before. Ten of the transformants obtained were analysed and were found to harbor the pBRES36COB vector, which was again indistinguishable from the original vector used for transformation, as shown by analysis of the restriction enzyme digests. In these ten transformants the level of vitamin B$_{12}$ synthesis was determined as follows.

Frozen cultures of *Propionibacterium* transformants 1 through 10, as well as a control strain containing only the vector plasmid pBRESP36B$_2$, were inoculated in 100 ml flasks containing 50 ml of BHI (Brain Heart Infusion) medium (Difco) and incubated for 72 hrs at 28° C. without shaking. From this preculture 4 ml we transferred to 200 ml of production medium consisting of Difco yeast extract 15 g/l, a Nalactate 30 g/l. KH$_2$PO$_4$ 0.5 g/l, MnSO$_4$ 0.01 g/l, and CoCl$_2$ 0.005 g/l in a 500 ml shake flask and incubated at 28° C. for 56 hrs without shaking, followed by 43 brs in a New Brunswick rotary shaker at 200 rpm.

Vitamin B$_{12}$ titres were measured using a known HPLC method[5]. Nine out of 10 transformants showed an approx. 25% higher vitamin B$^{12}$ production than the control strain.

EXAMPLE 6
Stability of the Plasmids

All three shuttle vectors pBRESP36A, pBRESP36B1, and pBRESP36B2 were stably maintained over 30 generations of culturing of the respective transformants: no loss of erythromycin resistance was observed as determined by viability counts on selective (erythromycin containing) and non-selective agar plates. The structural stability of the plasmid in transformant population after 30 generations was established by plamid DNA isolation and characterisation by restriction enzyme mapping as described above: only restriction fragments similar to those of the authentic plasmid were observed.

EXAMPLE 7
Database Sequence Homology Analysis for Predicted Polypeptide Encoded by the First Open Reading Frame (SEQ ID. No 2) MDSFETLFPESWLPRKPLASAEKS GAYRHVTRQRALELPYIEANPLVMQSLVITDRDASDA DWAADLAGLPSPSYVSMNRVTTTGHIVYALKNPVCL TDAARRRPINLLARVEQGLCDVLGGDASYGHRIT KNPLSTAHATLWGPADALYELRALAHTLDEIHAL PEAGNPRRNVTRSTVGRNVTLFDTTRMWAYRAVR HSWGGPVAEWEHTVFEHIHLLNETTIAD The above 227 amino acid sequence (ORF1) was aligned and compared with several other protein sequences (target NBRF-PIR, release PIR R52.0 March 1997, cut-off 45, KTUP:2).

With a protein from *Mycobacterium fortuitum* plasmid pAL 5,000 (JS0052) a match of 37.1% was found over 194 amino acids (INIT-167.292) With a protein from *Corynebacterium glutamicum* (S32701) a match 32.0% over 125 amino acids was found (INIT 125, 116). A match of 29.9% over 221 amino acids 86, 259) was found with the ColE2 protein from *E. coli* (SO4455) Precisely the same match over the same number of amino acids was found for the ColE3 protein, also from *E. coli* (SO4456).

EXAMPLE 8
Database Sequence Homology Analysis for Predicted Polypeptide Encoded by the Second Reading Frame (SEQ ID. No. 3) MTTRERLPRN GYSIAAAAKK LGVSESTVKR WTSEPREEFV ARVAARHARI RELRSEGQSM RALAAEVGVS VGTVHYALNK NRTDA The second protein (ORF2) was also aligned and compared with another protein, using the sane parameters and software as described for Example 7. This sequence however is only 85 amino acids in length The ORF2 sequence was compared with a protein from *Mycobacteium fortuitum* (S32702) and a 53.3 match over 75 amino acids was found (INIT 207, 207).

EXAMPLE 9
Functional Analysis of Plasmid p545

In order to improve the vector system further, the plasmid fictions essential for replication and stability were delineated more precisely through deletion of large regions of the original plasmid p545. The result, a smaller cloning vector, will allow the use of the p545 based vector system for cloning larger DNA fragments.

To this end vector pBRESP36A (FIG. 2) was digested with SsiII and BclI, resulting in a 1.7 kb and a 6.5 kb fragment. The 1.7 kb fragment, in fact the 1.6 kb AlwNI-BclI fragment of plasmid p545, was replaced by a synthetic duplex DNA, composed of SEQ. ID. No. 12 and SEQ. ID. No. 13 with SsiII and BclI compatible ends and a number of unique restriction enzyme recognition sites.

SEQ. ID. No. 12 5' GGAGATCTAGATCGATATCTCGAG 3'

SEQ. ID. No. 13 5' GATCCTCGAGATATCGATCTAGATC TCCGC 3'

The following restriction enzyme recognition sites were supplied in this way:

SstII (restored). BglII, XbaI, ClaI, EcoRV, XhoI, (BclI 13 is not restored). The ligation mixture was transferred to *E. coli*, and transformant were selected containing a vector of the expected composition. The vector was named pBRESAΔS-B. Subsequent successful transformation of *P. freudenreichii* strain ATCC6207 with this vector indicated that the 1.6 kb region between AlwNI and BclI in p545 is not essential for replication of the plasmid.

A further deletion was made by removal of the 240 bp corresponding to the region between SalI and BclI in plasmid p545. This was achieved by digestion of pBRESAΔS-B with SalI-SstI, and SstI-XhoI respectively, and isolation of the 1.3 kb SAlI-SstI fragment, and the 6.6 kb SstI-XhoI fragment. The fragments were ligated, and the ligation mixture was transferred to *P. freudenreichii*. ATCC6207, yielding numerous transformants. The newly derived construct, named pBreSAAS-S, was isolated and its structure confirmed by restriction enzyme mapping.

Thus all essential information for replication of plasmid p$^{545}$ is located on a fragment of 1.7 Xb delimited by the restriction sites SalI and AlwNI and encompassing the predicted replication proteins encoded by ORF1 and ORF2, and that 18 kb can be deleted without obviously disturbing replication or stability of the plasmid.

EXAMPLE 10

Expression of a Chloramphenicol Resistance Gene from Corynebacterium.

A chloramphenicol resistance gene (cmi from Corynebacterium[18] has been identified as encoding a chloramphenicol export protein. This gene was inserted in the *Propionibacterium-E. coli* shuttle vector pBRESP36B2. This vector was digested with BglII and HindIII, and with BglII and HpaI respectively. The 2.9 kb BglII-HindIII and 52 kb BglII-HpaI fragments were isolated.

The fragment containing the cmi gene, including its own promoter, was obtained by digestion with PvuII and HindIII, and the 3.3 kb fragment containing. The gene was isolated. The two vector-specific fragments and the cml fragment were ligated: PvuII and HpaI ends are blunt, thus inserting the cml gene as well as restoring the ermE gene of the parent vector. The ligation mixture was transferred to *E. coli*, and a transformant was selected, in which the vector contained the correct cml insert. The vector was named pBRESBCM.

Transformation or *P. freudenreichii* ATCC6207 with this vector, and selection on plates containing 10 μg/ml erythromycin or 5 μg/ml chloramphenicol, yielded eythromycin and choramphenicol resistant colonies, respectively, indicating that apart from the erythromycin resistance gene (shown earlier with the *Propionibacterium-E. coli* vectors), also the chloramphenicol resistance gene is expressed in *Propionibacterium*. Transformants could be cultivated in liquid medium containing up to 20 μg/ml chloramphenicol.

EXAMPLE 11

Expression of Lipase (gchA) Gene form *P. acnes*

To illustrate efficient cloning and expression of an extracellular protein using the present vector system, a lipase gene gehA from *P. acnes* was used[19]. Vector pUL6001, harbouring gehA on XhoI fragment, was digested with XhoI, and the 2.75 kb fragment containing the gene was isolated. Vector pBRESAΔS-B (from Example 9) was linearized by XhoI, and the ends dephosphorylated using Calf Intestine Phosphatase to avoid self ligation. Linearized vector and the gehA containing fragment were ligated and the ligation mixture was transferred to *E. coli* Transformants were analysed by restriction enzyme analysis for the presence of the correct recombinant plasmid named pBRESALIP. This plasmid was subsequently transferred to *P. freudenreichii* ATCC6207. Transformants were screened for the expression of the lipase gene using agar plates containing tributyrin as the indicator for increased lipase expression *P. freudenreichii* transformants harbouring pBRESALIP showed significantly increased halo sizes in this assay as compared to untransformed strain or strains transformed with the parent vector.

REFERENCES

1. Altschul et al J. Mol. Biol. 215:403–410 (1990)
2. Bibb et al. Gene 38, 215(1985)
3. Bibb et al., Mol. Microbiol. 14(3). S33 (1984)
4. Birnboim and Doly, Nucleic Acids Res. 7, 1513 (1979)
5. Blache, Anal. Biochem. 189, 24 (1990)
6. DeMan et al, J. Appl. Bateriol. 36, 130 (1960)
7. Deveraux et al, Nucleic Acids Research. 12:387–395 (1984)
8. Labidi et al, Plasmid 27, 130 (1992)
9. Rehberger and Glatz, Appl. Environ. Microbiol. 59, 83 (1990)
10. Rossi et al, Res Microbiol. 147, 133 (1996)
11. Sambrook et al, Molecular Cloning, Cold Spring Harbor Laboratory Press (1989)
12. Sattler et al, J. Bact. 177, 1564(1995)
13. Southern, J. Mol. Biol. 98, 503 (1975)
14. Stolt and Stoker, Microbiol. 142, 2795 (1996)
15. Thompson et al, Gcu c20, 51 (19U2)
16. Uchijama and Weishum, Gene 38, 103 (1985)
17. de Vries et al, J. Gen. Microbiol. 71, 515 (1972)
18. Tauch et al, Plasmid 40(2): 126(1998)
19. Miskin et al, Microbiol 143, 1745 (1997)

SUMMARY OF SEQUENCES

1. DNA sequence of plasmid LMG 16545 (CBS 101022). 3.6 kb.
2. amino acid of protein of ORF1 (303 residues, bases 273–1184).
3. amino acid of protein of ORF2 (85 residues, bases 1181–1438).
4–13. DNA primers/oligonucleotides Names & Fax Nos

| | |
|---|---|
| Daniel & Cia, Brazil | 00 55 21 524 3344 |
| Osler, Hoskin & Harcourt, Canada | 00 1 613 235 2867 |
| CCPIT, China | 86 10 68587610/11/12/13 |
| Traplova, Hakr, Kubar, Prague | +420 2 6671 0172 |
| S.B.G. & K Patent and Law Offices, Hungary | 00 36 1 34 24 323 |
| Reinhold Cohn and Partners, Israel | 00 972 3 560 6405 |
| Mcssrs Sigurjonsson, Iceland | +354 562 2633 |
| Aoyama & Partners | (81) 6-6949-0361 |
| Y S Chang, South Korea | (822) 556 5377 or 556 5969 |
| Uhthoff, Gomez etc, Mexico | (52) 52 08 83 87 |
| Oslo Patentkontor A/S, Norway | 00 47 2 255 3088 |
| Polservice, Poland | 00 48 22830 00 76 |
| Patenservis Bratislava A.S, Slovakia | +421 7 4487 2075 |
| Ella Cheong & Miranda, Singapore | 00 65 337 0031 |
| Stock Industrial etc, Turkey | (212) 324 3118 or 3119 |
| McDonnell, Boehnen etc, USA | 00 1 312 913 0002 |

What is claimed is:

1. A process for the production of vitamin B12 (cobalamin), the process comprising culturing a *Propionibacterium* host cell under conditions in which the vitamin is produced and, if necessary, isolating the vitamin, wherein the *Propionibacterium* host cell contains a polynucleotide comprising
   (a) a sequence that is selected from the group consisting of:
      (i) SEQ ID NO: 1 or the complement thereof,
      (ii) a sequence from SEQ ID NO: 1 that corresponds to either the 1.7 kb fragment of SEQ ID NO: 1 delineated by restriction sites Sal I and AlwNI or nucleotides 1 to 1800 of SEQ ID NO: 1; and
      (iii) a sequence that is at least 95% homologous to a sequence as defined under (i) or (ii) and which retains the ability to autonomously replicate in *Propionibacterium*; and
   (b) a sequence that is an endogenous gene of a *Propionibacterium* in belonging to the vitamin $B_{12}$ biosynthesis pathway or a pathway directly linked to the vitamin $B_{12}$ biosynthesis pathway operatively linked to a control sequence which is capable of providing for expression of the gene.

2. A process according to claim 1, wherein the endogenous gene of a *Propionibacterium* is the cobA gene.

3. A process according to claim 1 wherein the polynucleotide is comprised in a vector.

4. A process according to claim 3 wherein the vector is a plasmid.

5. A process according to claim 1 wherein the polynucleotide comprises a selectable marker.

6. A process according to claim 1 wherein the polynucleotide is capable of autonomously replicating in *E. coli*.

7. A process according to claim 1 wherein the host cell is a *P. freudenreichii, P. jensenii, P. theonii* or *P. acidipropionici* cell.

8. A process according to claim 1 wherein the vitamin $B_{12}$ is isolated from the host cell or from the culture medium.

* * * * *

SEQUENCE LISTING

<160> NUMBER OF SEQ ID NOS: 13

<210> SEQ ID NO 1
<211> LENGTH: 3555
<212> TYPE: DNA
<213> ORGANISM: Propionibacterium freudenreichii LMG16545
<220> FEATURE:
<221> NAME/KEY: CDS
<222> LOCATION: (273)..(1184)

<400> SEQUENCE: 1

```
gtcgaccctg acagccggcg agcagttcag gcgaagatcg cacagctgcg cgaggaacta      60
gccgcaatgc ccgaacacgc cccagccatc ccttggagca ggtggcagcg tcaggggagt     120
cgggggatgt ttggcagggg atgtggaaag agagttcgct ttgctcacat ggctcaaccg     180
ggtaactaac tgtatatggg tcttcgtcgc ccactttgaa cacgccgagg aatggaccac     240
gctgaacgtg actcgcatgc ttcactgcat gt atg gat tcg ttc gag acg ttg      293
                                   Met Asp Ser Phe Glu Thr Leu
                                    1               5 ttc cct gag agc tgg ctg cca cgc aag ccg ctg gcg tca gcc gag aag      341
Phe Pro Glu Ser Trp Leu Pro Arg Lys Pro Leu Ala Ser Ala Glu Lys
        10                  15                  20 tct ggg gcg tac cgg cac gtg act cgg cag agg gcg ctg gag ctg cct      389
Ser Gly Ala Tyr Arg His Val Thr Arg Gln Arg Ala Leu Glu Leu Pro
    25                  30                  35 tac atc gaa gcg aac ccg ttg gtc atg cag tcc ttg gtc atc acc gat      437
Tyr Ile Glu Ala Asn Pro Leu Val Met Gln Ser Leu Val Ile Thr Asp
40                  45                  50                  55 cga gat gct tcg gat gct gac tgg gcc gca gac ctc gct ggg ctg cct      485
Arg Asp Ala Ser Asp Ala Asp Trp Ala Ala Asp Leu Ala Gly Leu Pro
                60                  65                  70 tca ccg tcc tac gtg tcc atg aac cgt gtc acg acc acc gga cac atc      533
Ser Pro Ser Tyr Val Ser Met Asn Arg Val Thr Thr Thr Gly His Ile
            75                  80                  85 gtc tat gcc ttg aag aac cct gtg tgt ctg acc gat gcc gcg cgg cga      581
Val Tyr Ala Leu Lys Asn Pro Val Cys Leu Thr Asp Ala Ala Arg Arg
        90                  95                  100 cgg cct atc aac ctg ctc gcc cgc gtc gag cag ggc cta tgc gac gtt      629
Arg Pro Ile Asn Leu Leu Ala Arg Val Glu Gln Gly Leu Cys Asp Val
    105                 110                 115 ctc ggc ggc gat gca tcc tac ggg cac cgg atc aca aag aac ccg ctc      677
Leu Gly Gly Asp Ala Ser Tyr Gly His Arg Ile Thr Lys Asn Pro Leu
120                 125                 130                 135 agc acc gcc cat gcg acc ctc tgg ggc ccc gca gac gcg ctc tac gag      725
Ser Thr Ala His Ala Thr Leu Trp Gly Pro Ala Asp Ala Leu Tyr Glu
                140                 145                 150 ctg cgc gcc ctc gca cac acc ctc gac gag atc cac gca ctg ccg gag      773
Leu Arg Ala Leu Ala His Thr Leu Asp Glu Ile His Ala Leu Pro Glu
            155                 160                 165 gca ggg aac ccg cgt cgc aac gtc acc cga tca acg gtc ggc cgc aac      821
Ala Gly Asn Pro Arg Arg Asn Val Thr Arg Ser Thr Val Gly Arg Asn
        170                 175                 180 gtc acc ctg ttc gac acc acc cgc atg tgg gca tac cgg gcc gtc cgg      869
Val Thr Leu Phe Asp Thr Thr Arg Met Trp Ala Tyr Arg Ala Val Arg
    185                 190                 195 cac tcc tgg ggc ggc ccg gtc gcc gaa tgg gag cac acc gta ttc gag      917
His Ser Trp Gly Gly Pro Val Ala Glu Trp Glu His Thr Val Phe Glu
200                 205                 210                 215
```

-continued

| | |
|---|---|
| cac atc cac cta ctg aac gag acg atc atc gcc gac gaa ttc gcc aca<br>His Ile His Leu Leu Asn Glu Thr Ile Ile Ala Asp Glu Phe Ala Thr<br>                          220                         225                         230 | 965 |
| ggc ccc ctc ggc ttg aac gaa ctt aag cac tta tct cga tcc att tcc<br>Gly Pro Leu Gly Leu Asn Glu Leu Lys His Leu Ser Arg Ser Ile Ser<br>                235                         240                       245 | 1013 |
| cga tgg gtc tgg cgc aac ttc acc ccc gaa acc ttc cgc gca cgc cag<br>Arg Trp Val Trp Arg Asn Phe Thr Pro Glu Thr Phe Arg Ala Arg Gln<br>      250                       255                       260 | 1061 |
| aaa gcg atc agc ctc cgt gga gca tcc aaa ggc ggc aaa gaa ggc ggc<br>Lys Ala Ile Ser Leu Arg Gly Ala Ser Lys Gly Gly Lys Glu Gly Gly<br>        265                       270                       275 | 1109 |
| cac aaa ggc ggc att gcc agt ggc gca tca cgg cgc gcc cat acc cgt<br>His Lys Gly Gly Ile Ala Ser Gly Ala Ser Arg Arg Ala His Thr Arg<br>280                       285                       290                       295 | 1157 |
| caa cag ttc ttg gag ggt ctc tca tga ccacacgtga acgtctcccc<br>Gln Gln Phe Leu Glu Gly Leu Ser<br>                       300 | 1204 |
| cgcaacggct acagcatcgc cgctgctgcg aaaaagctcg gtgtctccga gtccaccgtc | 1264 |
| aagcggtgga cttccgagcc acgcgaggag ttcgtggccc gcgttgccgc acgccacgcg | 1324 |
| cggattcgtg agctccgctc ggagggtcag agcatgcgtg cgattgctgc cgaggtcggg | 1384 |
| gtttccgtgg gcaccgtgca ctacgcgctg aacaagaatc gaactgacgc atgaccgtaa | 1444 |
| cgccgcacga tgagcatttt cttgatcgtg caccgcttgg cactacgttc gcgtgcggtt | 1504 |
| gcacagtgcg cgccacgttc ttatcctgcg gccattgtgg ctacagccaa tggggggcat | 1564 |
| cagcaacgga cgttgaaccc ggtgggcaag tgttactcag ggggacatgc ccagtctgcg | 1624 |
| gcgctcggat tgacggtatg gcagtcgtgc atgcggcccc accgtcaaac tcattcaggt | 1684 |
| atcagtgaga accctcatgg caccccctcg tgacacgttc tcgttgcgat cagctgctgt | 1744 |
| gcgtgcgggc gtgagcgttt ctacgctgcg gcgcaggaaa tcagagcttg aggctgccgg | 1804 |
| agcgacggta gaccgtccg gttgggtggt gccactgcgt gcactcaagg tcgttttttgg | 1864 |
| ggtgtcagat gagacctcga atgcgcccgg tcatgacgct gagttagtgg cgcagctgcg | 1924 |
| ctctgagaac gagttttttac ggcgtcaggt cgagcagcag gcgcgcacga tcgaacggca | 1984 |
| ggctgaggca cacgcggtgg tctcagcgca gctcacacgg gttggccagc ttgaggccgg | 2044 |
| cgacgcagca gcaccgacac tggcacccgt tgaaaggccg gctccgcgac ggcggtggtg | 2104 |
| gcagcgtcgg tagcggtcag gatcgctctg gcgtgacgag tgtgtctggc agtgcgaaca | 2164 |
| gttgctcgac cagtggcagc agaagcgaga tcgctgcgtg gtgctgttcc tcggtcagtt | 2224 |
| cgtcgaggac tggcgggtct tgctgcgtcc agccgatcgc ctcggcggcc aaggtcagtt | 2284 |
| ccaagctgtg ccaacgcaca cgcccctcgg ctgacagctg agtctcgaac tgtgcaactg | 2344 |
| gaccggccgg aagatgcacg ttgccgaggt cgtgagtggc caagcgcacg tcaaagagtg | 2404 |
| ctgcttcgta gccgcgcaga atggcagtg ctcggtcgat tcggatcggc ctgcccaggt | 2464 |
| acattccggg ccgcttgatg aacgcctccg cgtagaagcg caccgttctc ggcccggcct | 2524 |
| cgtgatctgt cactgtgcac gctcctctcg atggttctcg acgctaccgg agaccaccga | 2584 |
| cgttcatgcc cagcgcagcg acctgaaagg accaagccga gttagccgtg ctaaccgtat | 2644 |
| agcttgctcc gtcgcctctg agggcaacca cctgcgcagc aggtgggcgg cagcccgcgc | 2704 |
| gcaagcgcct accgggtttg ggcacagccc ataaatcaac gcctccggtg ttgaagcgat | 2764 |
| cgtgtgtcac gattgctatg cttgctaccc cttcagggtt ttcgtataca caaatcaagt | 2824 |
| tttttcgtat acgctaatgc catgagtgag catctactgc acggcaagcc cgtcaccaac | 2884 |

```
gagcagattc aggcatgggc agacgaggcc gaggccggat acgacctgcc caaactcccc    2944
aagccacggc gcggacgccc gcccgtagga gacggtccgg gcaccgtcgt acccgtgcgt    3004
ctcgacgcgg ccaccgttgc cgctctcaca gaacgagcaa cagccgaggg catcacgaac    3064
cgttcagacg cgatccgagc cgcagtccac gagtggacac gggttgcctg acctccacga    3124
ctcagcacgc aagcactacc aacgagaccg gctcgacgac acggccgtgc tctacgcggc    3184
cacccacgtt ctcaactccc ggccactcga cgacgaagac gacccgcgcc gctggctcat    3244
gatcggaacc gacccagcag gccgcctact cgaactcgtc gcactgatct acgacgacgg    3304
ctacgaactg atcatccacg caatgaaagc ccgcacccaa tacctcgacc agctctaacc    3364
aagaaaggaa cctgatgagc gaccagctag acacgaccg caactacgac ccgatgatct     3424
tcgacgtgat gcgcgagacc gcgaaccgcg tcgtcgccac gtacgttgca tgggaagatg    3484
aagccgctga tccccgcgag gctgcgcact ggcaggccga gcgattccgc acccggcacg    3544
aggtgcgcgc c                                                          3555
```

<210> SEQ ID NO 2
<211> LENGTH: 303
<212> TYPE: PRT
<213> ORGANISM: Propionibacterium freudenreichii LMG16545

<400> SEQUENCE: 2

```
Met Asp Ser Phe Glu Thr Leu Phe Pro Glu Ser Trp Leu Pro Arg Lys
1               5                   10                  15

Pro Leu Ala Ser Ala Glu Lys Ser Gly Ala Tyr Arg His Val Thr Arg
            20                  25                  30

Gln Arg Ala Leu Glu Leu Pro Tyr Ile Glu Ala Asn Pro Leu Val Met
        35                  40                  45

Gln Ser Leu Val Ile Thr Asp Arg Asp Ala Ser Asp Ala Asp Trp Ala
    50                  55                  60

Ala Asp Leu Ala Gly Leu Pro Ser Pro Ser Tyr Val Ser Met Asn Arg
65                  70                  75                  80

Val Thr Thr Thr Gly His Ile Val Tyr Ala Leu Lys Asn Pro Val Cys
                85                  90                  95

Leu Thr Asp Ala Ala Arg Arg Pro Ile Asn Leu Leu Ala Arg Val
            100                 105                 110

Glu Gln Gly Leu Cys Asp Val Leu Gly Gly Asp Ala Ser Tyr Gly His
        115                 120                 125

Arg Ile Thr Lys Asn Pro Leu Ser Thr Ala His Ala Thr Leu Trp Gly
    130                 135                 140

Pro Ala Asp Ala Leu Tyr Glu Leu Arg Ala Leu Ala His Thr Leu Asp
145                 150                 155                 160

Glu Ile His Ala Leu Pro Glu Ala Gly Asn Pro Arg Arg Asn Val Thr
                165                 170                 175

Arg Ser Thr Val Gly Arg Asn Val Thr Leu Phe Asp Thr Thr Arg Met
            180                 185                 190

Trp Ala Tyr Arg Ala Val Arg His Ser Trp Gly Pro Val Ala Glu
        195                 200                 205

Trp Glu His Thr Val Phe Glu His Ile His Leu Leu Asn Glu Thr Ile
    210                 215                 220

Ile Ala Asp Glu Phe Ala Thr Gly Pro Leu Gly Leu Asn Glu Leu Lys
225                 230                 235                 240

His Leu Ser Arg Ser Ile Ser Arg Trp Val Trp Arg Asn Phe Thr Pro
```

```
                    245                 250                 255
Glu Thr Phe Arg Ala Arg Gln Lys Ala Ile Ser Leu Arg Gly Ala Ser
            260                 265                 270
Lys Gly Gly Lys Glu Gly Gly His Lys Gly Gly Ile Ala Ser Gly Ala
        275                 280                 285
Ser Arg Arg Ala His Thr Arg Gln Gln Phe Leu Glu Gly Leu Ser
    290                 295                 300

<210> SEQ ID NO 3
<211> LENGTH: 85
<212> TYPE: PRT
<213> ORGANISM: Propionibacterium freudenreichii LMG16545

<400> SEQUENCE: 3

Met Thr Thr Arg Glu Arg Leu Pro Arg Asn Gly Tyr Ser Ile Ala Ala
 1               5                  10                  15

Ala Ala Lys Lys Leu Gly Val Ser Glu Ser Thr Val Lys Arg Trp Thr
                20                  25                  30

Ser Glu Pro Arg Glu Glu Phe Val Ala Arg Val Ala Ala Arg His Ala
            35                  40                  45

Arg Ile Arg Glu Leu Arg Ser Glu Gly Gln Ser Met Arg Ala Ile Ala
        50                  55                  60

Ala Glu Val Gly Val Ser Val Gly Thr Val His Tyr Ala Leu Asn Lys
 65                  70                  75                  80

Asn Arg Thr Asp Ala
            85

<210> SEQ ID NO 4
<211> LENGTH: 59
<212> TYPE: DNA
<213> ORGANISM: Artificial Sequence
<220> FEATURE:
<223> OTHER INFORMATION: Synthetic Duplex DNA designed to link EcoRI
      and AvaI

<400> SEQUENCE: 4
aattcaagct tgtcgacgtt aacctgcagg catgcggatc cggtaccgat atcagatct        59

<210> SEQ ID NO 5
<211> LENGTH: 59
<212> TYPE: DNA
<213> ORGANISM: Artificial Sequence
<220> FEATURE:
<223> OTHER INFORMATION: Synthetic Duplex DNA designed to link EcoRI
      and AvaI

<400> SEQUENCE: 5
ccgaagatct gatatcggta ccggatccgc atgcctgcag gttaacgtcg acaagcttg        59

<210> SEQ ID NO 6
<211> LENGTH: 24
<212> TYPE: DNA
<213> ORGANISM: Artificial Sequence
<220> FEATURE:
<223> OTHER INFORMATION: Synthetic DNA designed to create Acc65I and
      BglII ends

<400> SEQUENCE: 6
gtaccggccg ctgcggccaa gctt                                              24

<210> SEQ ID NO 7
<211> LENGTH: 24
```

```
<212> TYPE: DNA
<213> ORGANISM: Artificial Sequence
<220> FEATURE:
<223> OTHER INFORMATION: Synthetic DNA designed to create Acc65I and
      BglII ends

<400> SEQUENCE: 7
gatcaagctt ggccgcagcg gccg                                              24

<210> SEQ ID NO 8
<211> LENGTH: 35
<212> TYPE: DNA
<213> ORGANISM: Artificial Sequence
<220> FEATURE:
<223> OTHER INFORMATION: Synthetic primer for erythromycin resistance

<400> SEQUENCE: 8
aaactgcagc tgctggcttg cgcccgatgc tagtc                                  35

<210> SEQ ID NO 9
<211> LENGTH: 76
<212> TYPE: DNA
<213> ORGANISM: Artificial Sequence
<220> FEATURE:
<223> OTHER INFORMATION: Synthetic primer for erythromycin resistance

<400> SEQUENCE: 9
aaactgcagc agctgggcag gccgctggac ggcctgccct cgagctcgtc tagaatgtgc       60
tgccgatcct ggttgc                                                       76

<210> SEQ ID NO 10
<211> LENGTH: 32
<212> TYPE: DNA
<213> ORGANISM: Artificial Sequence
<220> FEATURE:
<223> OTHER INFORMATION: Synthetic primer for cobA

<400> SEQUENCE: 10
ctagtctaga caccgatgag gaaacccgat ga                                     32

<210> SEQ ID NO 11
<211> LENGTH: 36
<212> TYPE: DNA
<213> ORGANISM: Artificial Sequence
<220> FEATURE:
<223> OTHER INFORMATION: Synthetic primer for cobA

<400> SEQUENCE: 11
cccaagcttc tcgagtcagt ggtcgctggg cgcgcg                                 36

<210> SEQ ID NO 12
<211> LENGTH: 24
<212> TYPE: DNA
<213> ORGANISM: Artificial Sequence
<220> FEATURE:
<223> OTHER INFORMATION: Synthetic DNA for stability testing

<400> SEQUENCE: 12
ggagatctag atcgatatct cgag                                              24

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA for stability testing
```

```
<400> SEQUENCE: 13
gatcctcgag atatcgatct agatctccgc                                    30
```